United States Patent [19]
Johansson et al.

[11] Patent Number: 4,642,305
[45] Date of Patent: Feb. 10, 1987

[54] EYE DROPS COMPOSITION

[75] Inventors: Elof Johansson; Lena Öhman, both of Upsala, Sweden

[73] Assignee: Pharmacia AB, Upsala, Sweden

[21] Appl. No.: 734,268

[22] PCT Filed: Oct. 24, 1984

[86] PCT No.: PCT/SE84/00354
§ 371 Date: May 14, 1985
§ 102(e) Date: May 14, 1985

[87] PCT Pub. No.: WO85/01875
PCT Pub. Date: May 9, 1985

[30] Foreign Application Priority Data
Oct. 25, 1983 [SE] Sweden ............................... 8305864

[51] Int. Cl.$^4$ .............................................. A61K 31/56
[52] U.S. Cl. ................................................ 514/182
[58] Field of Search ................... 424/14; 514/178, 182

[56] References Cited
U.S. PATENT DOCUMENTS
4,186,184 1/1980 Zaffaroni .............................. 424/14

Primary Examiner—Elbert L. Roberts
Attorney, Agent, or Firm—Fred Philpitt

[57] ABSTRACT

An eye drops composition containing estradiol-17beta dissolved therein or in a crystalline form, said composition being suitable for treating chronic catarrh disorders of the ocular conjunctiva, that is chronic conjunctivitis simplex.

9 Claims, 2 Drawing Figures

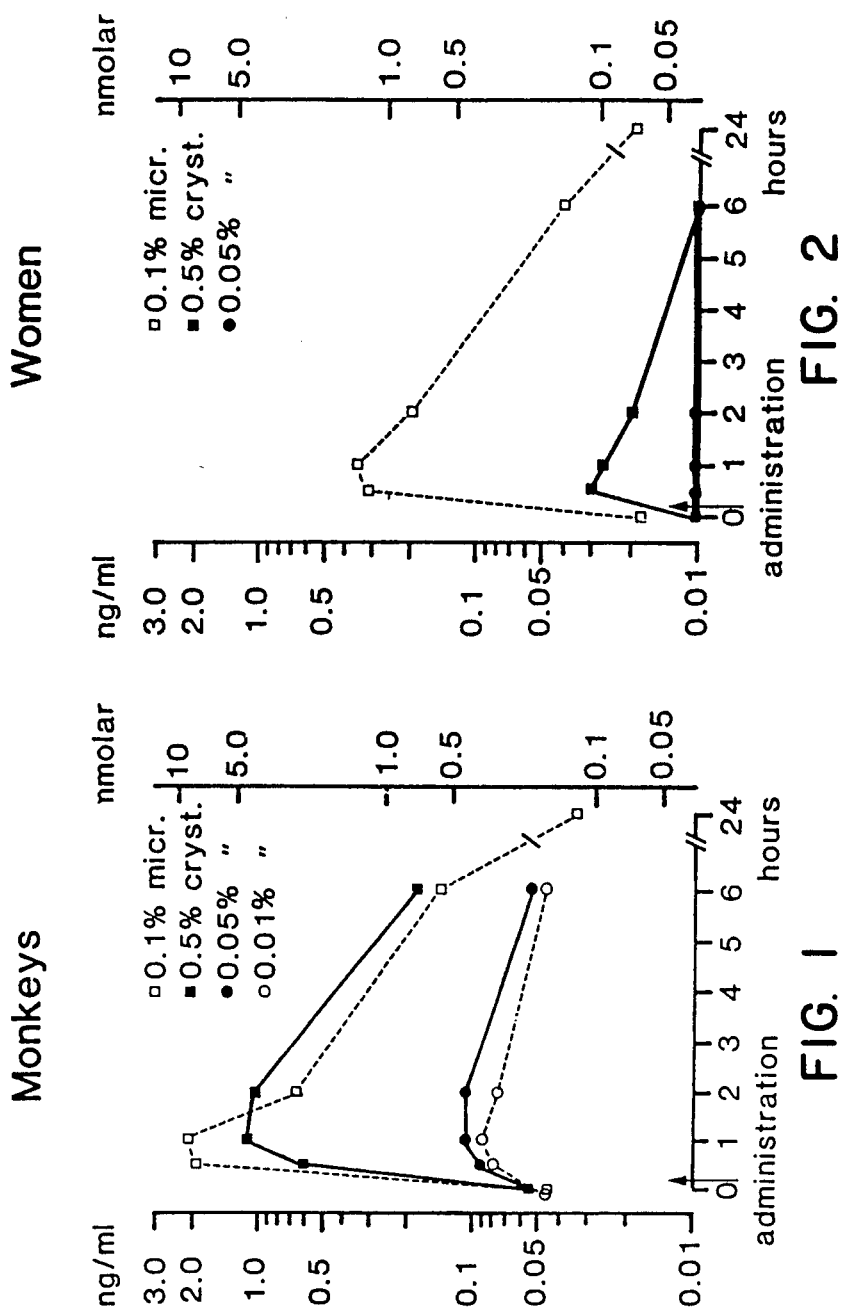

EYE DROPS COMPOSITION

The present invention is concerned with an eye drops composition containing estradiol-17beta in a dissolved or crystalline form for the treatment of chronic eye catarrh, that is chronic conjunctivitis simplex.

Chronic catarrh of the ocular conjunctiva is a condition common in middle-aged and elderly persons, especially in postmenopausal women (ages above about 45–50). Such a catarrh is apt to cause a great deal of discomfort to the patient. The eyes feel dry, "gritty" and irritated, which is a disagreeable condition, even though it does not really imply any serious damage to the eyes. As regards drug preparations for treating this condition, the preparations used up till now have generally been found to be inefficient. In certain cases some degree of alleviation may be obtained with agents having a weak cauterizing and/or decongestant effect. Also, ointments, having a lubrication effect, or viscous preparations capabel of forming a thin protective film over the eye may occasionally decrease the symptoms.

We have now found, in accordance with the present invention, that an effective means of treating chronic eye catarrh disorders is an eye drops composition containing estradiol17beta in a therapeutically active and physiologically acceptable amount.

Oral administration of estrogen has been suggested by Holly et al in Surv. Ophthalmol 22(2) (1977) 69-87 for treatment of keratoconjunctivitis sicca, that is a different type of eye disorder.

The hormone estradiol-17beta as a crystalline powder is almost insoluble in water. In our eye drops composition this hormone compound may be present in a crystalline, microcrystalline or dissolved state. We have found a suitable particle size to be one within the range of 1 to 25 micrometers, preferably 2 to 10 micrometers. The desired particle size and size distribution of the bulk of the particle mass, i.e. at least 90% thereof, can be obtained by mechanical working, such as e.g. grinding, followed by one or more screening steps. The mechanical procedure chosen should preferably be one that gives substantially smooth particle surfaces, to thus avoid frictional damage on the tissues of the eye. In view of the fact that there is only a very small space available in the conjunctiva for accommodating lacrimal fluid and eye drops, the amount of active compound, that can actually be administered, will depend largely on the concentration of the compound in the composition. The upper limit of concentration is set by the risk of an undesired increase of the hormone level in the blood, with a concomitant undersired systemic effect. In our experience this means, as applied to the case where estradiol-17beta is administered in a particulate form, that its concentration should not exceed about 0.05% by weight. A lower limit would be in this case around 0.005% by weight.

As mentioned above estradiol-17beta is almost insoluble in water; so, if this hormone is to be administered in a dissolved state, it has to be dissolved in a medium suitable therefor. Substances, which have been known for a long time to be solvents for steroid hormone compounds of this type, are for instance solutions of cyclodextrins. A number of cyclodextrin compounds have been described; for example, dimethyl beta-cyclodextrin is said to have advantageous properties for forming inclusion complexes with e.g. estrone (DE No. 3118218). It is imperative that the solvent chosen—whether this be a solution containing cyclodextrin, a derivative thereof or some other solvent—should be one, that does not to any substantial degree reduces the effect of the hormone. It is also imperative of course that neither the solvent nor the hormone-solvent complex should be liable to produce undersirable reactions in the eye. In these cases, preferred concentrations are within the range of from 0.001 to 0.01% by weight.

The composition according to the present invention is a sterile aqueous solution containing estradiol-17beta in a particulate or dissolved form. In addition the composition may contain such components as are known and commonly employed in artificial tear solutions, for example buffer and salt systems, such as isotonic phosphate-buffered sodium chloride, polymeric substances and preservatives. Among the examples of polymeric substances set forth may be mentioned especially cellulose derivatives such as methyl cellulose, hydroxyethyl cellulose and hydroxypropyl cellulose; dextran and dextran derivatives; hyaluronic acid; and polyvinyl alcohol. A review of such commercially available eye drops compositions is presented in e.g. the Physicians' Desk Reference for Ophthalmology 1980/81, Publ. Charles E. Baker, Jr. (Med. Econ. Comp., Litton).

To prepare a composition according to the invention, estradiol-17beta may be added in either particulate form of dissolved form to an eye drops solution of a known type, with due attention to the requirements discussed above. Alternatively the composition may be prepared in that the particulate or dissolved hormone is mixed with one or more of the components normally employed for eye drops preparations, or with components having similar properties.

A suitable dosage is about 0.5 to 25 microgram of hormone per eye per day, preferably to be given as two separate administrations.

The present invention thus comprises an eye drops composition for treating irritated and dry eyes, said composition containing estradiol-17beta in a therapeutically active and physiologically acceptable amount. According to one embodiment the hormone is present in the composition in the form of particles having a size of 1 to 20 micrometers, preferably 2 to 10 micrometers, and having a concentration of 0.005 to 0.05% by weight, preferably 0.008 to 0.03% by weight.

According to another embodiment the hormone is present in a dissolved state, its concentration being 0.001 to 0.01% by weight; it is preferably dissolved in an aqueous solution containing cyclodextrin or a derivative thereof.

One aim of the invention is also to provide a method of treating chronic conjunctivitis simplex in which an 0.5 to microgram daily dose of estradiol-17beta is applied to the patient's eye by way of an eye drops composition according to the invention.

EXAMPLES

I. (a) Preparation of eye drops compositions containing estradiol-17beta 0.17 g (2,6-di-o-methyl)beta cyclodextrin was dissolved in 200 ml of physiological saline. 20.25 mg estradiol-17beta (DAK) was then added and the mixture was stirred for 3 hours. The solution was then filtered and the concentration of the hormone in the filtrate was determined at 280 nanometers to be 0.0092% by weight.

(b) A 0.5% (w/w) aqueous solution of methyl cellulose was prepared. Varying amounts of estradiol-17beta (Sigma) in crystalline or micronized form was then added and the suspension was thoroughly mixed.

II. Tests performed with monkeys

The tests were run with five anesthetized female monkeys of which two were ovariectomized and three menstruating. 50 microliters of eye drops compositions prepared according to Example I(b) were applied to the monkeys' eyes, whereupon the level of this hormone in the blood was recorded for the next 24 hours. Hormone analyses were carried out in accordance with Edquist and Johansson, Acta Endocrin. 71 (1972) 716. Analysis results are set forth in FIG. 1 "Mean plasma levels of estradiol-17beta after topical administration of two eye drops". As will be seen from this Figure, estradiol-17beta both as crystalline particles and micronized gave significantly increased levels in the blood when its concentration in the solution exceeded about 0.05% by weight.

III (a). Tests performed with human subjects; studies of hormone levels in the blood of healthy women An eye drops composition was prepared similarly as in Example I(b), and drops having a volume of 25 microliters were applied to the eyes of healthy postmenopausal women. Analysis results are set forth in FIG. 2 "Mean plasma levels of estradiol-17beta after topical administration of two eye drops". The tests show that concentrations exceeding about 0.05% by weight resulted in a significantly increased hormone level in the blood.

III (b) Tests performed with chronic conjunctivitis patients

Patients suffereing from chronic conjunctivitis simplex were treated twice daily with eye drops (25 microliters) containing 0.05% by weight of crystalline estradiol-17beta in an 0.5% aqueous solution of methyl cellulose. Already after about 1 to 2 weeks the condition of the eyes had clearly improved. It was observed that the treatment had not caused any hormone level increase in the blood of the patients and no general side effects were observed.

In order to demonstrate the local effect on the ocular conjuctiva biopsies were taken therefrom, at first before the start of the treatment and then again after one month of treatment, for microscopic studies of the changes (if any), that had occurred in this mucous membrane. Samples were taken from the inside of the lower lid after local anesthesia. A significant change of the epithelium of the conjunctiva could be demonstrated in patients treated with the eye drops preparation.

We claim:

1. An eye drop composition for the treatment of chronic conjunctivitis simplex comprising estradiol-17beta in a concentration of from 0.001 to 0.01% by weight, dissolved in a solution of cyclodextrin or cyclodextrin derivative.

2. A method of treating chronic conjunctivitis simplex which comprises applying to the eye a daily dose of 0.5 to 25 micrograms of estradiol-17beta.

3. A method according to claim 2 wherein estradiol-17beta is applied in crystalline or microcrystalline form.

4. A method according to claim 3 in which the particle size in said crystalline or microcrystalline form is in the range of from 1 to 25 micrometers.

5. A method according to claim 3 in which the particle size in said crystalline or microcrystalline form is in the range of from 2 to 10 micrometers.

6. A method according to claim 2 in which estradiol-17beta is applied in a dissolved state.

7. A method according to claim 6 in which estradiol-17 is dissolved in a solution of cyclodextrin or a cyclodextrin derivative.

8. A method of treating chronic conjunctivitis simplex which comprises applying to the eye an eye drop composition comprising estradiol-17beta and at least one water-soluble component selected from the group consisting of cellulose derivatives, dextran, dextran derivatives, hyaluronic acid, polyvinyl alcohol and physiological saline, in a daily dose of from 0.5 to 25 micrograms of estradiol-17beta.

9. A method according to claim 8 wherein estradiol-17beta is applied in crystalline or microcrystalline form.

* * * * *